United States Patent [19]

Murib

[11] 4,229,587

[45] Oct. 21, 1980

[54] PROCESS FOR PREPARING AROMATIC ESTERS

[75] Inventor: Jawad H. Murib, Cincinnati, Ohio

[73] Assignee: National Distillers and Chemical Corporation, New York, N.Y.

[21] Appl. No.: 973,498

[22] Filed: Dec. 26, 1978

[51] Int. Cl.² .............................................. C07C 67/05
[52] U.S. Cl. ..................................... 560/131; 252/456; 252/464; 252/467; 260/410.5; 560/1; 560/193; 560/241
[58] Field of Search ..................... 560/131, 241, 193, 1; 260/410.5; 252/464, 467, 456

[56] References Cited

U.S. PATENT DOCUMENTS

| | | | |
|---|---|---|---|
| 4,016,200 | 4/1977 | Anoda et al. | 560/131 |
| 4,045,373 | 8/1977 | Innes et al. | 252/469 |

*Primary Examiner*—Vivian Garner
*Attorney, Agent, or Firm*—Kenneth D. Tremain

[57] ABSTRACT

A process for preparing aromatic esters by oxyacylation which comprises contacting benzene or an aryl alkyl compound with a carboxylic acid and oxygen in the vapor phase in the presence of a catalytically effective amount of a catalyst comprising an oxide of uranium and at least one oxide selected from the group consisting of arsenic, antimony and bismuth oxide.

8 Claims, No Drawings

PROCESS FOR PREPARING AROMATIC ESTERS

BACKGROUND OF THE INVENTION

This invention relates to the preparation of aromatic esters by the catalyzed oxyacylation reaction of benzene or aryl alkyl compounds, oxygen and a carboxylic acid in the vapor phase.

The preparation of aromatic esters by the vapor phase reaction of an aromatic compound, carboxylic acid and oxygen in the presence of a noble metal containing catalyst, especially palladium, is well-known. Thus, for example, with acetic acid, when using benzene, phenyl acetate is obtained, and when using toluene, benzyl acetate is prepared. U.S. Pat. No. 3,275,680 granted to Holzrichter et al. discloses such a reaction and is hereby incorporated by reference.

Over the years, the oxyacylation reaction has been the subject of an extensive research effort because, for one reason, the noble metal catalyst is very expensive and it is an important cost factor in the process. U.S. Pat. No. 3,275,680, Great Britain Pat. Nos. 1,017,938 and 1,117,595 each describe the preparation of benzyl acetate and other benzyl esters wherein an alkyl-substituted phenyl compound such as toluene is reacted in the gaseous phase with an oxygen containing gas, for example, air, acetic acid, and an alkali metal acetate in the presence of a catalyzst containing palladium metal supported upon a suitable substrate. Candian Pat. No. 820,352 describes a similar process wherein the catalyst contains metallic palladium and gold, and an alkali metal salt as sodium acetate. Great Britain Pat. No. 1,328,058 describes a process for preparing benzyl acetate by the reaction of toluene, oxygen and acetic acid in the gaseous phase at an elevated temperature in the presence of a supported catalyst system containing an oxide, hydroxide or carboxylate of palladium and bismuth, or in the case of palladium, the metal itself, and a hydroxide, carbonate or carboxylate of an alkali metal compound. Other metals, including gold and/or copper, or compounds of these metals which do not contain halogen, sulfur or nitrogen, may be added so as to affect the activity and selectivity of the catalyst.

It has now been found that benzene, toluene and other aryl alkyl compounds may be catalytically oxyacylated to phenyl acetate, benzyl acetate and other such esters without the need for using a noble metal catalyst.

It is an object of this invention to provide an improved oxyacylation process for the preparation of aromatic esters from benzene or aryl alkyl compounds. Other objects and advantages will become apparent from the following description.

SUMMARY OF THE INVENTION

It has now been discovered that aromatic esters may be prepared by oxyacylation by contacting benzene or an aryl alkyl compound, oxygen and carboxylic acid in the vapor phase at elevated temperatures in the presence of a catalyst comprising an oxide of uranium and at least one oxide selected from the group consisting of arsenic, antimony and bismuth oxides. A preferred embodiment of the invention is to employ a catalyst comprising an oxide of uranium and an oxide of antimony. In general, the alkyl group of the aryl compound is about $C_1$ to $C_4$ and the alkyl compound may be substituted by one or two alkyl groups.

DETAILED DESCRIPTION OF THE INVENTION

The starting compound for the present process is benzene or an aryl alkyl compound, i.e. toluene, xylene, cumene, mesitylene, and the like.

The oxyacetylation of xylene with acetic acid yields, as the primary product, tolyl acetate (cresyl acetate). The preferred aryl alkyl compound for use in this process is toluene.

The carboxylic acids useful in the invention contain about 2 to about 8 carbon atoms, preferably 2 to 6 carbon atoms, and include propionic, butyric and isobutyric acids. The preferred carboxylic acid for use in this process is acetic acid. Aliphatic carboxylic acids having two or more -COOH groups may also be employed.

In the following description of preferred embodiments, reference is principally made to the oxyacetylation of benzene with acetic acid, to phenyl acetate, but it should be understood that the process description is applicable to substituted benzenes and aryl alkyl compounds, as hereinbefore described.

Benzene may be used in pure form or in diluted form, such as, for example, in the form of a mixture containing up to about 50% of diluents, usually inert hydrocarbons, e.g., heptane, hexane or cyclohexane or may contain impurities normally present in commercial grades of this reactant. The preferred carboxylic acid for use herein, acetic acid, is advantageously provided as glacial acetic acid, although the use of aqueous solutions thereof may be used.

The oxygen may be pure oxygen gas or alternatively, an oxygen-containing gas mixture such as air or air enriched with oxygen. In additional to these materials the oxygen may contain other inert diluents such as carbon dioxide, nitrogen and the like.

The catalyst herein comprises an oxide of uranium and at least one oxide selected from the group consisting of arsenic, antimony and bismuth. The aforestated oxides can exist in any of their oxidation states and be made from compounds of any oxidation state and specifically include uranium dioxide, uranyl uranate, uranium trioxide, the trioxides, tetroxides and pentoxides of arsenic, antimony and bismuth, and mixtures of these oxides. The atomic ratio of uranium to antimony, bismuth and/or arsenic can vary over wide limits and advantageously is within the ratio of about 50:1 to 1:99. A ratio of 10:1 to 1:10 is preferred. U.S. Pat. No. 3,198,750 discloses a suitable catalyst containing mixed antimony oxide and uranium oxide and a method for preparing the catalyst, said patent being hereby incorporated by reference.

While it is not necessary to provide the catalysts of this invention with a support, it is generally advantageous to deposit the catalysts upon a carrier such as any of the known and conventional catalyst carrier materials since catalytic efficiency will thereby be significantly improved. Thus, the catalysts herein can advantageously be supported upon silica, alumina, zirconia, silica alumina, silicon carbide, alundum and inorganic silicate in an amount, by weight of metal of the supported catalyst, of about 1 percent to about 90 percent, preferably about 10 to 50 percent. A preferred catalyst contains about 5% to 30% arsenic, bismuth or antimony, preferably antimony and 1% to 20% uranium, by weight of the supported catalyst.

The catalyst may be prepared by known techniques, e.g., contacting a metal salt solution with the support, drying and calcining in an oxidizing atmosphere, e.g., in the presence of an air sweep. A range of drying temperature of 100°–120° C. and a calcining temperature of 350°–900° C. may be suitably employed. Non-supported catalysts may be prepared by precipitation of the soluble salt or salts from solution by, e.g., neutralization with aqueous ammonia solution, filtration, washing, drying and calcining.

A preferred method for preparing a catalyst comprises treating an extruded or pelletized support with an aqueous solution containing uranyl nitrate and/or antimony pentachloride and concentrated hydrochloric acid. The mixture is evaporated and the impregnated support is dried at 110°–120° C. for an additional 12 hours. Examples of suitable water soluble metal compounds which can be used in the preparation of the supported catalyst include uranyl nitrate, uranyl chloride, uranyl sulfate, uranyl tetrachloride, arsenic acid, antimony pentachloride and bismuth nitrate. The catalyst bed can be a fixed bed employing a large particulate or pelleted catalyst or in the alternative, a fluidized bed of catalyst can be utilized.

The catalyst may also contain promoters, such as oxides of molybdenum, thallium, bismuth, copper and silver which are useful, e.g., to improve the selectivity and reaction rate. The amount of promoter, by weight and metal on the supported catalyst, is generally within the range of about 0.1–10%, perferably about 0.5%–3.5%, e.g., 3%.

In general, an apparatus of the type suitable for carrying out reactions in the vapor phase can be used in carrying out the oxyacylation reaction of this invention. The reactor can be brought to the reaction temperature before or after the introduction of the reaction feed mixture. However, in a large-scale operation, it is preferred to carry out the process in a continuous manner and in such a system, the recirculation of unreacted reactants is contemplated.

The concentrations of benzene, carboxylic acid and oxygen used in the oxyacylation reaction can vary widely. The effective minimum concentration of cataylst will depend upon temperature, residence time and the particular composition of the catalyst employed. The mole ratios of oxygen to benzene to carboxylic acid fed to the reaction zone is not critical but it should be adjusted so that the mixture used is not in the explosive region. The stoichiometric ratio of benzene: carboxylic acid: oxygen is 2:2:1 and the relative proportions may vary widely. In general, the benzene may be used in large excess to improve the selectivity to the ester. Broadly stated, in volume percent, based on the total content of benzene, carboxylic acid and oxygen, the oxygen is about 1%–50%, the carboxylic acid is about 1%–77% and the benzene is about 1%–98%. A preferred range is about 1% to 20% oxygen, 2% to 40% carboxylic acid and 45% to 97% benzene. The feed may also be diluted with nitrogen or other inert gas to maintain the mixture outside the explosive limits. Water may be employed in the reaction and may be present in amounts up to about 25 volume %. The water may be added to the reactor as a separate recycle stream or vaporized recovered unreacted carboxylic acid.

In general, the temperature in the reaction zone is about 200°–450° C., perferably about 250°–400° C., although higher or lower temperatures may be employed.

In my copending applications filed concurrently herewith it is disclosed and claimed that the reaction process is dependent mainly upon the olefin employed and the pressure in the reaction zone. Thus, for example, in the application entitled "Process for Preparing Gamma-Lactones" U.S. Application No. 972,857, filed Dec. 26, 1978 when alpha-olefins are reacted at low pressure, up to about 40 psig, gamma-lactones are formed, such as gamma-butyrolactone from etylene. At high pressures, e.g., above about 40 psig, in the application entitled "Process for Preparing Ethylene Glycol Esters" U.S. Application No. 972,855, filed Dec. 26, 1978, oxyacylation of ethylene produces ethylene glycol esters and oxyacylation of higher olefins e.g., propylene as described in the application entitled "Process for Preparing Unsaturated Esters" U.S. Application No. 972,856 filed Dec. 26, 1978 produces allyl acetate as a major product. In the instant process, a wide range of pressures may be empolyed in the oxyacylation zone. Pressures up to about 1000 psig, or higher, may be employed but will not normally be used due to equipment limitation and increased cost. A preferred range is about atmospheric to 200 psig, e.g., atmospheric to about 80 psig.

The reaction time will depend largely upon the concentration of reactants and therefore, may suitably vary over a wide range. Flow rates are preferably adjusted so that the contact time is in the range of about 0.1 and 60 seconds, and preferably between about 1 and 5 seconds. The product from the reaction may then be recovered by known methods, e.g., extraction, distillation, etc.

The following examples are illustrative of the invention.

EXAMPLE 1

Preparation of catalyst

Extruded silica gel, 429.5 gram (g.) ($\frac{1}{8}$" diameter × $\frac{1}{4}$" long, 200 m$^2$/g surface area) was placed in a 2-liter beaker and treated with an aqueous solution containing 248.8 grams (g.) SbCl$_5$, 90.6 g. UO$_2$ (NO$_3$)$_2$.6H$_2$O and 210 g. concentrated HCL. While mixing, the mixture was heated to dryness on a hot plate. The resulting impregnated extrudates were calcined in air at 450° C. for twelve hours followed by calcining in air at 850° C. for an additional twelve hours.

EXAMPLE 2

A 30 milliliter (ml.) stainless steel reactor 10 centimeter (cm.) × 2 cm. (inside diameter) with a thermocouple was packed with 14.3 g. of the catalyst prepared above. A gaseous stream of 629 cubic centimeters (cc.)/minute of, by volume, 10% benzene, 10% acetic acid, 5% oxygen and 75% nitrogen was passed through the reactor and contacted with the catalyst at one atmosphere pressure and about 350° C. The reactor effluent was bubbled through a U-tube held at 0° C. The noncondensible gases were measured by a wet-test meter and a sample of the gaseous mixture was analyzed for oxygen and carbon oxides (CO and CO$_2$). Analysis of the condensate disclosed formation of phenyl acetate as established by gas-liquid chromatography and mass spectroscopy.

It will be apparent that many changes and modifications of the several features described herein may be made without departing from the spirit and scope of the invention. It is therefore apparent that the foregoing description is by way of illustration of the invention rather than limitations of the invention.

What is claimed is:

1. A process for the preparation of esters which comprises reacting benzene or an aryl alkyl compound wherein the alkyl group is about $C_1$ to $C_4$ with a $C_2$ to $C_8$ carboxylic acid and oxygen in the vapor phase at an elevated temperature in the presence of a catalytically effective amount of a catalyst consisting essentially of an oxide of uranium and at least one oxide selected from the group consisting of arsenic, antimony and bismuth oxides.

2. The process of claim 1 wherein the compound is benzene or toluene.

3. The process of claim 2 wherein the carboxylic acid is acetic acid.

4. The process of claim 3 wherein the catalyst is an oxide of uranium and an oxide of antimony.

5. The process of claim 4 wherein the catalyst is supported.

6. The process of claim 5 wherein the temperature is about 200°–450° C. and the pressure is atmospheric to 200 psig.

7. The process of claim 1 wherein the reaction temperature is about 200° to 450° C. and the pressure atmospheric to 200 psig.

8. A process for the preparation of esters which comprises reacting benzene or an aryl alkyl compound wherein the alkyl group is about $C_1$ to $C_4$ with a $C_2$ to $C_8$ carboxylic acid and oxygen in the vapor phase at an elevated temperature in the presence of a catalytically effective amount of a catalyst consisting essentially of an oxide of uranium and at least one oxide selected from the group consisting of arsenic, antimony and bismuth oxides and a promoter selected from the group consisting of oxides of molybdenum, thallium, copper and silver.

* * * * *